US00PP35386P2

(12) United States Plant Patent
Quero Garcia

(10) Patent No.: US PP35,386 P2
(45) Date of Patent: Sep. 19, 2023

(54) CHERRY TREE NAMED 'DENFER'

(50) Latin Name: *Prunus avium*
Varietal Denomination: Denfer

(71) Applicant: INRAE Institut National de Recherche pour l'agriculture, l'alimentation et l'environnement, Paris (FR)

(72) Inventor: Jose Quero Garcia, Villenave d'Ornon (FR)

(73) Assignee: INRAE Institut National de Recherche pour l'agriculture, l'alimentation et l'environnement, Paris (FR)

( * ) Notice: Subject to any disclaimer, the term of this patent is extended or adjusted under 35 U.S.C. 154(b) by 0 days.

(21) Appl. No.: 17/803,738

(22) Filed: Nov. 1, 2022

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./180, 181
See application file for complete search history.

*Primary Examiner* — Susan McCormick Ewoldt
(74) *Attorney, Agent, or Firm* — Michelle Bos Legal LLC

(57) ABSTRACT

A sweet cherry tree named 'Denfer' distinguished by its regular production of firm uniform fruit with good acid to sugar balance.

2 Drawing Sheets

Latin name: *Prunus avium.*
Variety denomination: 'Denfer'.

BACKGROUND AND SUMMARY OF THE VARIETY

The new sweet cherry tree named 'Denfer' originated as a seedling obtained from a controlled cross of 'Agoudel' (female parent, not patented) with 'Burlat' (male parent, not patented) carried out at Bordeaux, France in 1994. The seedling was first asexually propagated by grafting at Bordeaux, France in 2001 and subsequently observed over several growing seasons. The 'Denfer' sweet cherry tree was initially selected for its regular production of firm uniform fruit with good acid to sugar balance.

'Denfer' is distinguished from its parents and similar variety 'Folfer' (not patented) as set forth in Tables 1 through 3 below.

TABLE 1

Comparison of 'Denfer' to female parent 'Agoudel'

| Characteristic | 'Denfer' | 'Agoudel' |
|---|---|---|
| Time of beginning of fruit ripening | Medium | Late |
| Fruit firmness | Firm | Medium |

TABLE 2

Comparison of 'Denfer' to male parent 'Burlat'

| Characteristic | 'Denfer' | 'Burlat' |
|---|---|---|
| Time of beginning of fruit ripening | Mid to late June (15 to 18 days after 'Burlat') | Early |
| Fruit skin color | Strong red | Brown red |
| Fruit acidity | Medium | Low |

TABLE 3

Comparison of 'Denfer' to similar variety 'Folfer'

| Characteristic | 'Denfer' | 'Folfer' |
|---|---|---|
| Harvest maturity | Mid to late June (6 to 7 days after 'Folfer') | Mid June |
| Fruit firmness | Firm | Very firm |

The 'Denfer' sweet cherry tree has been found to retain its distinctive characteristics through successive asexually propagated generations.

BRIEF DESCRIPTION OF THE PHOTOGRAPHS

The accompanying photographs were obtained in 2022 at Parker, Washington. The tree shown was planted in 2015.

Figure 1:
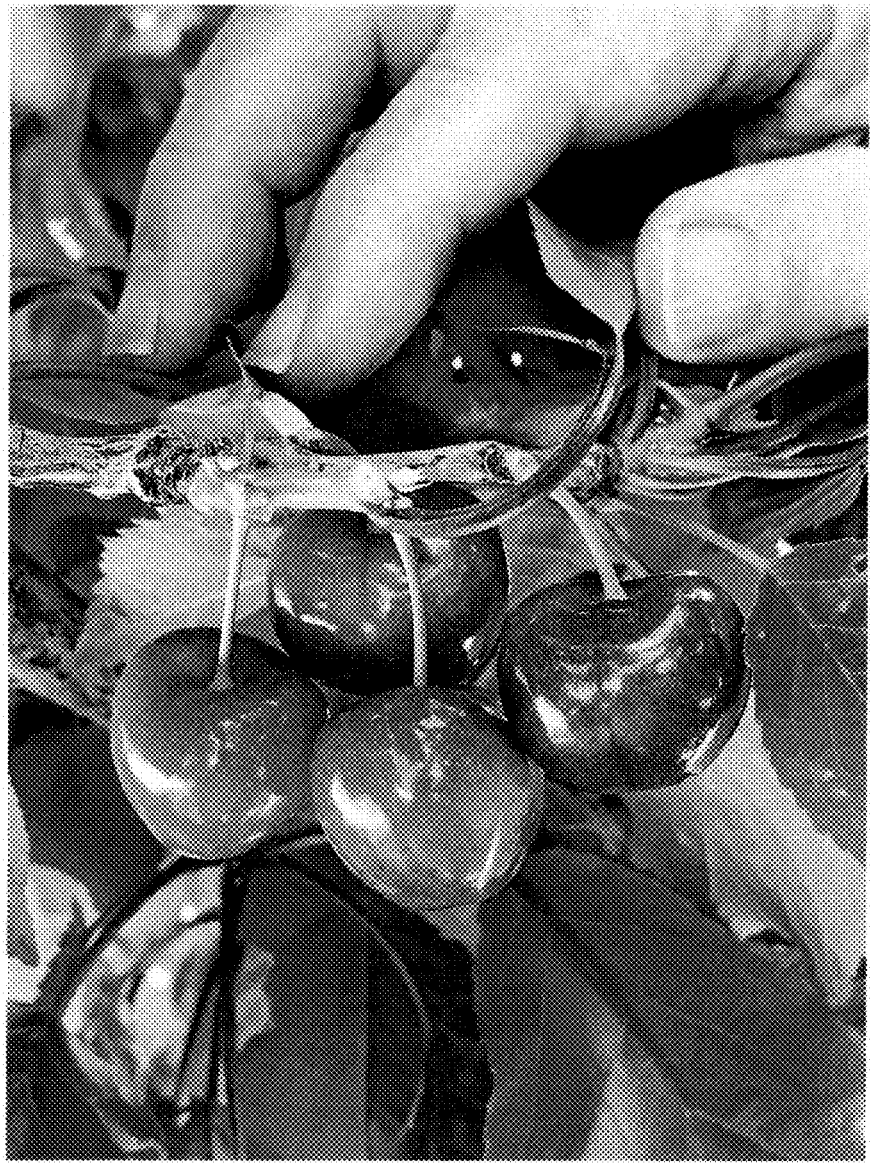
FIG. 1 shows 'Denfer' cherries and leaves on the tree.
Figure 2:
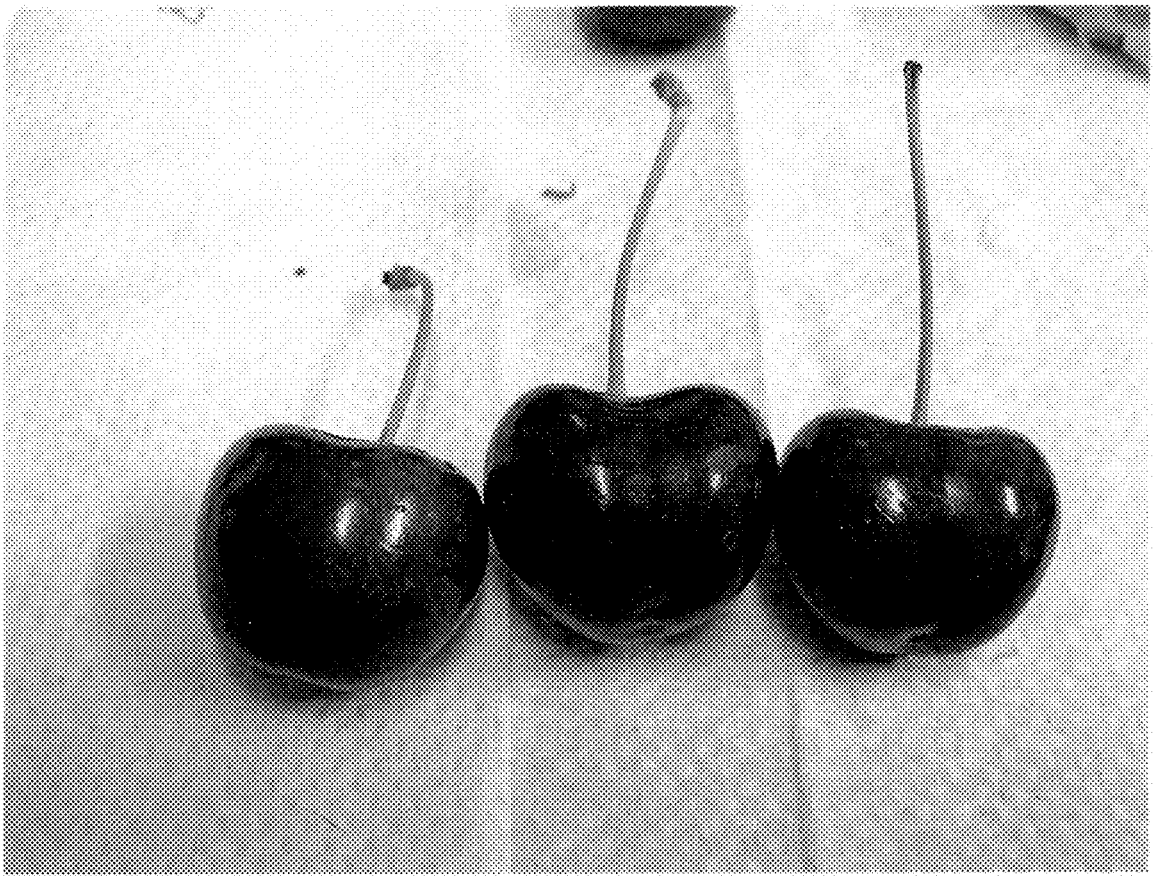
FIG. 2 shows 'Denfer' cherries.

The colors shown in the photographs may vary with lighting conditions. Color characteristics of the claimed plant should therefore be determined with reference to the observations described herein, rather than from the photographs alone.

DETAILED BOTANICAL DESCRIPTION

The following detailed botanical description is based on observations of 'Denfer' cherry trees growing on Maxma® 14 rootstock (not patented). The described trees were planted in 2015 at Parker, Washington. Observations were recorded during the 2022 growing season. The characteristics described will vary somewhat depending upon cultural practices and climatic conditions, and will vary with location and season. Quantified measurements are expressed as an average of measurements taken from a number of individual plants of the new variety. The measurements of any individual plant, or any group of plants, of the new variety may vary from the stated average. Color descriptions are made with reference to The R.H.S. Colour Chart, 4th ed. (Royal Horticultural Society, 2001).

Tree:

*Height*.—Approximately 3.6 m.
*Spread*.—Approximately 1.8 m.
*Vigor*.—Vigorous.
*Habit, shape*.—Semi-upright spreading.
*Density*.—Moderate.
*Cold hardiness*.—Hardy in area tested (USDA Hardiness Zone 6a).
*Heat tolerance*.—Heat tolerant in area tested.

Trunk:

*Trunk diameter at* 30 *cm above graft*.—9 cm.
*Bark texture*.—Rough.
*Bark color*.—Greyed-purple N187.
*Lenticel size*.—2 cm to 3 cm long.
*Lenticel color*.—Grey-brown 199D.
*Lenticel quantity*.—6 per $cm^2$.
*Productivity*.—Productive, regular bearer.

Branches:

*Length*.—1 m.
*Diameter*.—0.5 cm.
*Crotch angle*.—70 degrees.
*Bark color*.—Grey 201D.
*Bark texture*.—Smooth.
*Internode length*.—4 cm to 6 cm.
*Lenticel diameter*.—1 mm.
*Lenticel color*.—Yellow-orange 19C.
*Lenticel quantity*.—8 to 11 per 10 $cm^2$.

One year old shoot:

*Length*.—50 cm.
*Diameter*.—0.4 cm.
*Color*.—Yellow-green 145B.
*Internode length*.—5 cm to 6 cm.
*Lenticel diameter*.—1 mm.
*Lenticel color*.—Yellow-green 145D.
*Lenticel quantity*.—11 per 10 $cm^2$.

Flower buds:

*Stage described*.—Balloon stage.
*Quantity per spur*.—8 to 12.
*Shape*.—Ovoid.
*Apex shape*.—Rounded.
*Length*.—2.1 cm.
*Diameter*.—0.9 cm.
*Color*.—White NN155C.
*Date of bud burst*.—March 28 (2022 growing season).

Flowers:

*Diameter of fully open flower*.—36 mm.
*Depth of fully open flower*.—10 mm.
*Relative position of petal margins*.—Not touching.
*Pedicel length*.—23 mm.
*Pedicel diameter*.—2 mm.
*Pedicel color*.—Yellow green 146C.
*Date of first bloom*.—April 2 (2022 growing season).
*Date of full bloom*.—April 5 (2022 growing season).

Petals:

*Number per flower*.—5.
*Length*.—19 mm.
*Width*.—13 mm.
*Petal shape*.—Oval.
*Apex shape*.—Rounded.
*Base shape*.—Attenuate.
*Margin*.—Entire, ruffled.
*Upper surface color*.—White NN155D.
*Lower surface color*.—White NN155D.

Pistil:

*Pistil length*.—12 mm.
*Pistil color*.—Yellow-green 151C.
*Stigma diameter*.—2 mm.
*Stigma color*.—Grey-brown N199D.
*Style length*.—11 mm.
*Style color*.—Yellow-green 151C.
*Ovary length*.—5 mm.
*Ovary diameter*.—3 mm.
*Ovary color*.—Green 143B.

Sepals:

*Quantity per flower*.—5.
*Length*.—6 mm.
*Width*.—5 mm at base, 2 mm at tip.
*Shape*.—Broad base with rounded apex; margin entire.
*Color*.—Green 138C.

Leaves:

*Arrangement*.—Alternate.
*Length*.—17 cm.
*Width*.—8 cm.
*Form*.—Oval.
*Apex*.—Acute.
*Base*.—Cuneate.
*Margin*.—Serrate.
*Thickness*.—Medium.
*Texture of upper surface*.—Glabrous.
*Pubescence*.—Absent.
*Venation pattern*.—Pinnate.
*Upper surface color*.—Green 139B.
*Lower surface color*.—Green 139C.
*Vein color*.—Yellow-green N148D.
*Petiole length*.—5 cm.
*Petiole diameter*.—2 mm.
*Petiole color*.—Yellow-green N148D.
*Petiole pubescence*.—Absent.
*Petiole glands*.—Present.
*Gland length*.—2 mm.
*Gland width*.—1 mm.
*Gland color*.—Red 39A.

Fruit:

*Quantity per cluster*.—Usually 7 to 8.
*Relative size*.—Large to extra-large (9 row to 9½ row).
*Length*.—30 mm.
*Diameter at widest point*.—30 mm.
*Form, viewed from apex*.—Round.
*Form, viewed from suture side*.—Reniform, symmetrical.
*Suture depth*.—Shallow.
*Stalk cavity depth*.—2 mm.
*Stalk cavity diameter*.—5 mm.
*Base shape*.—Flat to depressed.
*Stem length*.—40 mm.
*Stem diameter*.—1 mm.
*Stem color*.—Primarily yellow-green 145A, with yellow-green 145D near fruit end and greyed-orange 164A near distal end.
*Stem adhesion to stone*.—Firmly adhered.

Fruit flesh:

*Firmness*.—Firm.
*Texture*.—Creamy, fine.
*Flavor*.—Sweet with pleasant acid/sugar balance.
*Juiciness*.—Very juicy.
*Brix*.—16%.
*Aroma*.—Mild.
*Flesh color*.—Red 42B with red 46B near stone.
*Juice color*.—Red 53C.

Fruit skin:

*Thickness*.—Medium.

*Texture*.—Smooth.

*Ground color*.—Red 44B.

*Over color*.—Red 46B.

*Lenticel quantity*.—Abundant.

Stone:

*Length*.—15 mm.

*Diameter*.—10 mm.

*Shape*.—Rounded, symmetrical.

*Surface texture*.—Smooth.

*Color*.—Orange 27A.

*Tendency to split*.—None.

Harvest maturity: Mid-season, 15 to 18 days after 'Burlat'.

*Number of picks*.—1.

*Harvest yield*.—About 20 metric tons per hectare when grown on a moderately vigorous rootstock; Variables such as rootstock, climate and planting density affect yield, which can range from 10 to 50 tons per hectare.

Use: Fresh consumption.

Susceptibility and resistance: No susceptibility or resistance to known pests or diseases has been observed to date.

Storageability: Good, 3 weeks in cold storage.

Shipping quality: Good.

The invention claimed is:

1. A new and distinct cherry tree named 'Denfer' substantially as illustrated and described herein.

* * * * *